(12) United States Patent
Chu

(10) Patent No.: US 6,613,548 B1
(45) Date of Patent: Sep. 2, 2003

(54) FUSION PRODUCTS CONTAINING INSOLUBLE PROTEINACEOUS TAG

(75) Inventor: Ruiyin Chu, Brookfield, WI (US)

(73) Assignee: Pierce Biotechnology, Inc., Rockford, IL (US)

( * ) Notice: Subject to any disclaimer, the term of this patent is extended or adjusted under 35 U.S.C. 154(b) by 0 days.

(21) Appl. No.: 09/744,604

(22) PCT Filed: Jul. 21, 1999

(86) PCT No.: PCT/US99/16409

§ 371 (c)(1),
(2), (4) Date: Jan. 24, 2001

(87) PCT Pub. No.: WO00/06763

PCT Pub. Date: Feb. 10, 2000

Related U.S. Application Data

(63) Continuation-in-part of application No. 09/127,051, filed on Jul. 31, 1998, now abandoned.

(51) Int. Cl.$^7$ ............................. C12P 21/04; C12N 9/06
(52) U.S. Cl. ....................... 435/69.7; 435/191
(58) Field of Search ............................ 435/69.7, 320.1, 435/191; 530/412; 536/23.2, 23.4

(56) References Cited

U.S. PATENT DOCUMENTS

| | | | |
|---|---|---|---|
| 4,870,023 A | 9/1989 | Fraser et al. | 435/235.1 |
| 5,110,729 A | 5/1992 | Maeda et al. | 435/69.1 |
| 5,861,274 A | 1/1999 | Evans et al. | 435/69.1 |

FOREIGN PATENT DOCUMENTS

| | | |
|---|---|---|
| WO | 96/01317 | 1/1996 |

OTHER PUBLICATIONS

Fujiwara et al. (1987) Comparative Biochemistry and Physiology, vol. 88 (2), pp. 467–469.*

Issemann et al. (1990) Nature, vol. 347, pp. 645–650.*

Alvares K et al: "Rat Urate Oxidase Produced by Recombinant Baculovirus Expression Formation of Peroxisome Crystalloid Core–Like Structures", Proceedings of the National Academy of Sciences of the United States, vol. 89, No. 11, 1992, pp. 4908–4912.

Chu Ruiyin et al: "Development of an insoluble fusion tag system: Enhanced expression and one–step purification of recombinant proteins." Molecular Biology of the Cell, vol. 9, No. Suppl., Nov. 1998, p. 477A; XP001124315; 38$^{th}$ Annual Meeting of the American Society of Cell Biology; San Francisco, CA, USA; Dec. 12–16, 1998.

Luckow et al. Signals Important for High–Level Expression of Foreign Genes in Autographa californica Nuclear Polyhedrosis Virus Expression Vectors. Virology. 1988, vol. 167, pp. 56–71, especially abstract p. 62, Figure 2.

Marumoto et al. Hyperproduction of Polyhedrin–IGF II Fusion Protein in Silkworm Larvae Infected with Recombinant *Bombyx mori* Nuclear Polyhedrosis virus. J. Gen Virol. 1987, vol. 68, pp. 2599–2606, especially abstract; p. 2600 "Methods", last paragraph.

Database CAPLUS, American Chemical Society, AN: 1991:179316, Issemann et al. 'Activation of a Member of the Steroid Hormone Receptor Superfamily by Peroxisome Proliferators,' abstract, Nature. 1990, vol. 347, No. 6294, pp. 645–650, see abstract.

* cited by examiner

*Primary Examiner*—Elizabeth Slobodyansky
(74) *Attorney, Agent, or Firm*—Quarles & Brady LLP

(57) ABSTRACT

A process is disclosed for the preparation of a recombinantly expressed fusion product comprised of a proteinaceous tag and a soluble protein of interest and the separation of the fusion product from the host cell in which it is expressed. The tag and in turn the fusion product is insoluble in the host cell lysate solution and the fusion product is separated therefrom by centrifugation or filtration.

1 Claim, 9 Drawing Sheets

FIG. 1
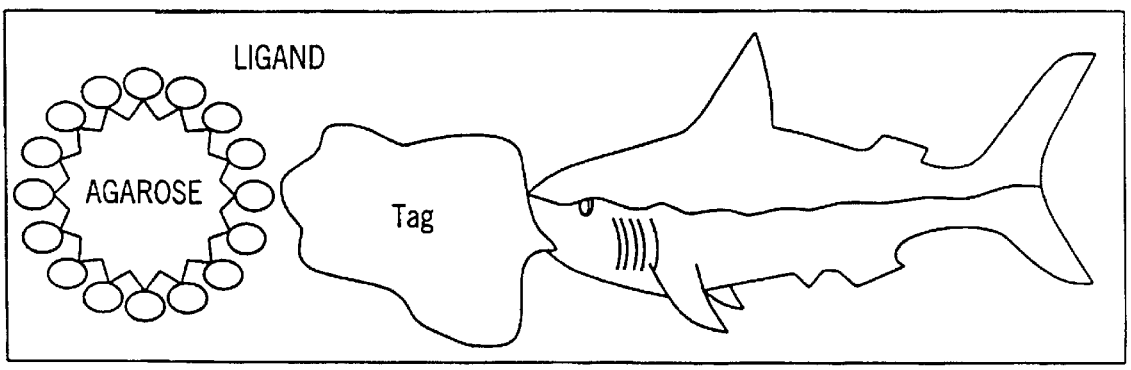
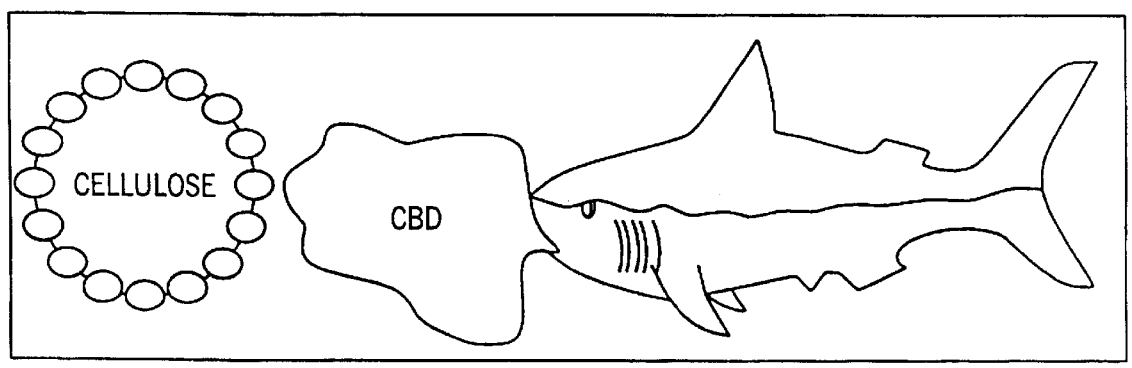
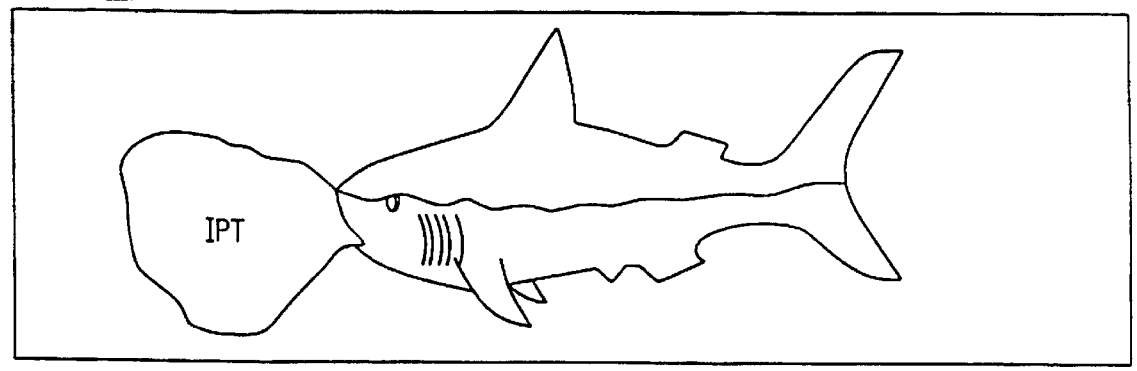

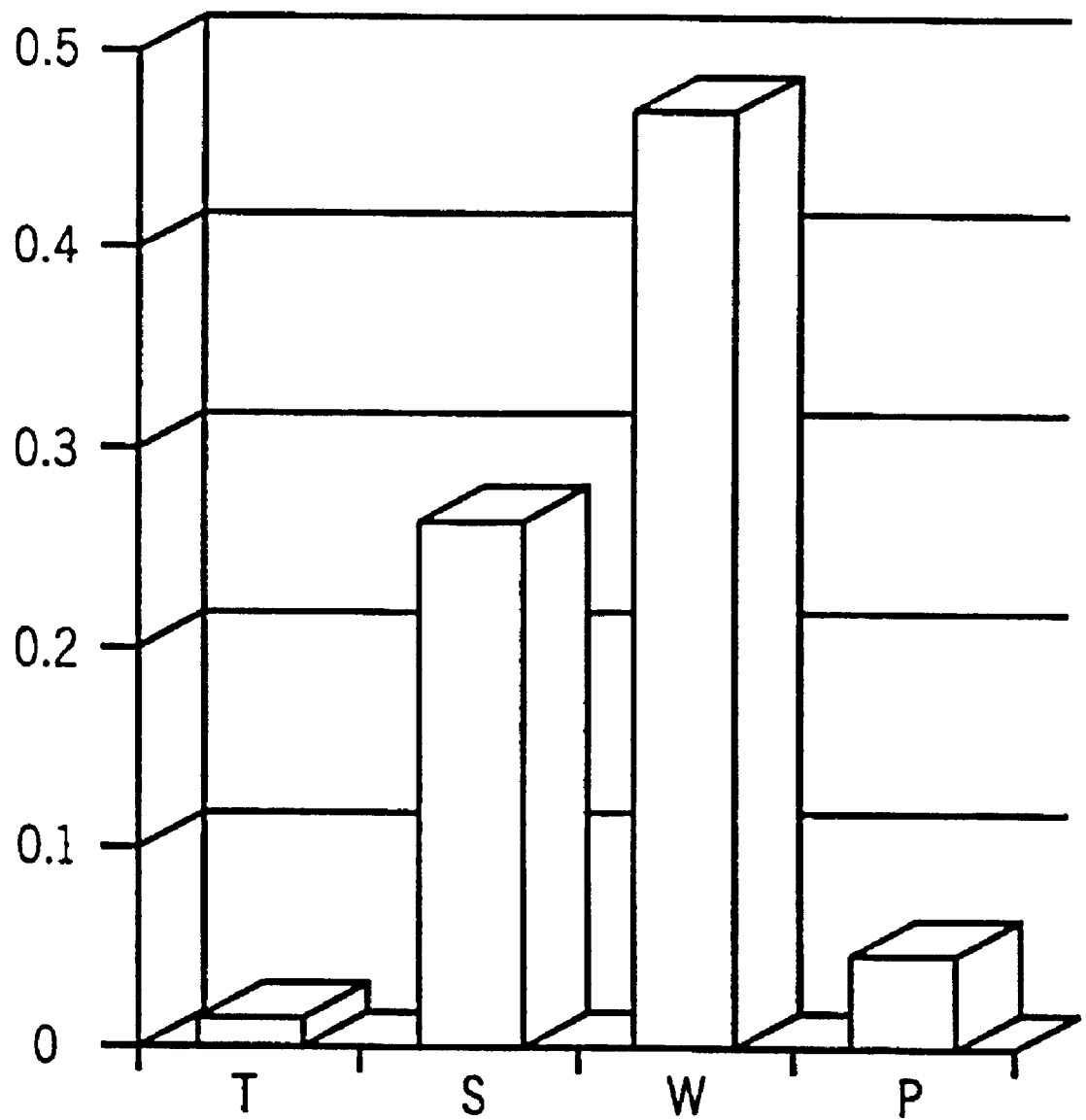

```
phd    1   MYTRYSYNPSLGRTYVYDNKFYKNLGSVIKNAKRKEHLALHEIEERT              47
uox    1   MAHYHDDYGKNDEVEFVRTGYGKDMVKVLHIQRDGKYHSIKEVATSVQLT            50 phd   48   LDPLERYVVAEDPFLGPGKNQK----LTLFKEIRIVKPDTMKLVVNWSG             92
uox   51   LRSKKDYLHGDNSDIIPTDTIKNTVHVLAKFKGIKSIETFAMNICEHFLS            100 phd   93   --KEFLR-------ETWTRFMED-----------SFP                        109
uox  101   SFSHVTRAHVHVEEVPWKRFEKNGVKHVHAFIHTPTGTHFCDVEQVRNGP            150 phd  110   IVNDQEIMDVFLVINMR------------PTRPNRCFRFLAQHALRC--            144
uox  151   PIHSGIKDLKVLKTTQSGFEGFIKDQFTTLPEVKDRCFATQVYCKWRYQ             200 phd  145   -----DPDYVPHEVIRIVEPVYVGNNN--EYRISLAKKGGGCPVMNLHSEY           188
uox  201   NRDVDFEATWGAVRDIVLKKFAGPYDRGEYSPSVQKTLYDIQVLTLS-QL            249 phd  189   THSFEEFINRVIWENFYKPIVYVGTDSGEEEILLELSLVFKIKEFAPDA             238
uox  250   PEIEDMEISLPNIHYFNIDMSKMGLIN--KEEVLLPLDNPYGKITGTVRR            297 phd  239   PLYNGPAY                                                      246
uox  298   KLPSRL                                                        303
```

FUSION PRODUCTS CONTAINING INSOLUBLE PROTEINACEOUS TAG

This application is a 371 of PCT/US99/16409 filed Jul. 21, 1999 which is a CIP of U.S. Ser. No. 09/127,051 filed Jul. 31, 1998 now abandoned.

FIELD OF INVENTION

The present invention relates to fusion products prepared by recombinant DNA procedures. The products are comprised of a soluble protein of interest and an insoluble proteinaceous tag. More particularly, the invention relates to the separation of such products from a cellular host in which the products have been expressed by utilization of the insolubility of the tag.

BACKGROUND OF THE INVENTION

Fusion techniques are popular for the preparation and recovery of recombinantly produced proteins of interest which are soluble in the host cell in which they are expressed. The proteins, which term herein also includes peptides, are of interest for research, diagnostic, or pharmaceutical use because of actual or supposed biological activity.

Preparation of fusion products involves ligating a fragment containing the DNA sequence coding for the protein of interest and a fragment containing the DNA sequence coding for a second protein commonly termed the "tag" into a vector. The vector is then introduced into a host cell, such as an insect cell, and the fusion product (protein of interest fused to the tag) is expressed. After expression, the cell is lysed thereby releasing the fusion product and other cellular proteins into the lysate solution. The fusion product is then separated from the lysate solution and subjected to further manipulation which can include cleavage and separation of the protein of interest from the tag.

A function of the tag in a fusion technique as above set forth is to facilitate separation of the fusion product from the host cell lysate solution. Separation techniques based on the well known principals of chromatography, in particular affinity chromatography, have commonly been employed; with affinity chromatography the tag functioning as a receptor having specific attraction for a ligand which typically is immobilized on a solid matrix. Contacting the lysate solution containing the fusion product with the solid matrix results in selective adsorption of the product onto the matrix. After washing the matrix to remove non-binding substances, the fusion product can be recovered by various elution techniques such as those based on pH, ionic strength or ligand competition.

Descriptions of the preparation of fusion products and the recovery and separation thereof by chromatographic techniques from host cell lysate solution are illustrated in the following U.S. patents and other publications, the disclosures of which are hereby incorporated by reference: 5,643,758; 5,654,176; 5,179,007; 4,879,236, 4,745,051, Biochem. J. (1986) 240, 1–12, Methods in Enzymology, Vol. 182, Guide to Protein Purification, and Methods in Molecular Biology, Vol. 59, Protein Purification Protocols. U.S. Pat. No. 5,496,934 is also so referenced as illustrating an affinity separation procedure where the tag (cellulose binding domain) binds directly to the matrix (cellulose), thus avoiding the use of a separate ligand bound to a matrix.

A problem associated with chromatographic techniques for the separation of fusion products from their cellular lysate solutions is that they are time consuming, involving as they do multiple steps including binding to a matrix, washing to remove non-specifically bound cellular components and subsequent elution. Also, the degree of binding of the fusion product to a matrix can be interfered with by various factors such as pH, ion concentration detergents and the like which can reduce the yield of fusion product.

SUMMARY OF THE INVENTION

One aspect of the present invention provides an improvement in those recognized processes for the preparation of a recombinantly expressed fusion product comprised of a proteinaceous tag and a soluble protein of interest and the subsequent separation of the fusion product from the host cell in which it is expressed. The process to which the improvement described herein pertains involves (1) preparing a vector containing the DNA sequence coding for the protein of interest and the DNA sequence coding for the tag, (2) introducing the vector into a host cell and expressing the fusion product, (3) lysing the host cell to liberate cellular proteins and then (4) utilizing the characteristics of the tag to separate the fusion product from the lysate solution. The improvement to this process provided by the present invention is the use, as the tag, of a protein which is insoluble in a normal lysate solution, which typically is at a pH of about 7–8. Accordingly, the fusion product containing the tag precipitates from the lysate solution and the precipitated fusion product can then be separated from the lysate solution by centrifugation or filtration.

Advantages accompanying the use of the process described herein include the fact that the separation of fusion product from lysate solution is a simple, one-step centrifugation or filtration procedure and that the expressed fusion product can be recovered in high yield from the host cell. An additional and particularly surprising advantage of the present process is that the level of expression or the fusion product in the host cell is increased above what would normally be expected.

An additional aspect of the present invention resides in providing a new and improved vector useful in practicing the foregoing process. Yet a further feature of this invention is to provide a recombinantly expressed fusion product comprised of a soluble protein of interest and an insoluble proteinaceous tag, the insolubility of the tag permitting the fusion product to precipitate from the host cell in which it is expressed.

A still further aspect of this invention resides in providing a easy process for cleaving the fusion product to separate the tag from the protein of interest and the subsequent recovery of the protein. In this respect, after the insoluble, precipitated fusion product is centrifuged or filtered from the lysate solution, it is dissolved in an aqueous medium at a basic pH of about 9–11, thus solubilizing the product. The tag can then be released from the protein of interest by cleaving with a site specific protease such as enterokinase. The pH of the solution containing the tag and protein is then reduced to about 7–8 by addition of an acidic buffer, thus causing precipitation of the tag which can then again be removed from solution by centrifugation or filtration; the protein of interest remaining in solution.

BRIEF DESCRIPTION OF THE DRAWINGS

FIG. 1. schematically represents three types of separation techniques for fusion products containing soluble proteins of interest (depicted by the fish) and a tag. The Type I system embodies most of the existing separation systems for such fusion products. An affinity ligand is immobilized on a matrix such as agarose to separate the product from solution utilizing, as a tag, an entity having specific affinity for the ligand. The Type II system uses cellulose to separate a fusion product containing as the tag, cellulose binding domain (CBD). The Type III system illustrates the present invention and uses an insoluble protein tag (IPT) to separate the fusion product from soluble cellular proteins.

FIG. 7. represents in bar graph form the detection of fusion protein by measuring uricase activity. IPTu-PPAR fusion protein from different purification steps was incubated with uric acid substrate in 0.1 M glycine (pH9.4) for 1 hour at 37° C. After incubation, $OD_{295}$ was measured using a spectrophotometer. The legend represents the following: T, total cell lysates; S, supernatant; W, washed supernatant; P, pellets.

FIG. 8 illustrates the similarity of the amino acid sequences of uricase (SEQ ID NO:10) and polyhedrin (SEQ ID NO:9) accomplished using the MACVECTOR program from Oxford Molecular Group.

DESCRIPTION OF THE INVENTION

Figure 2:
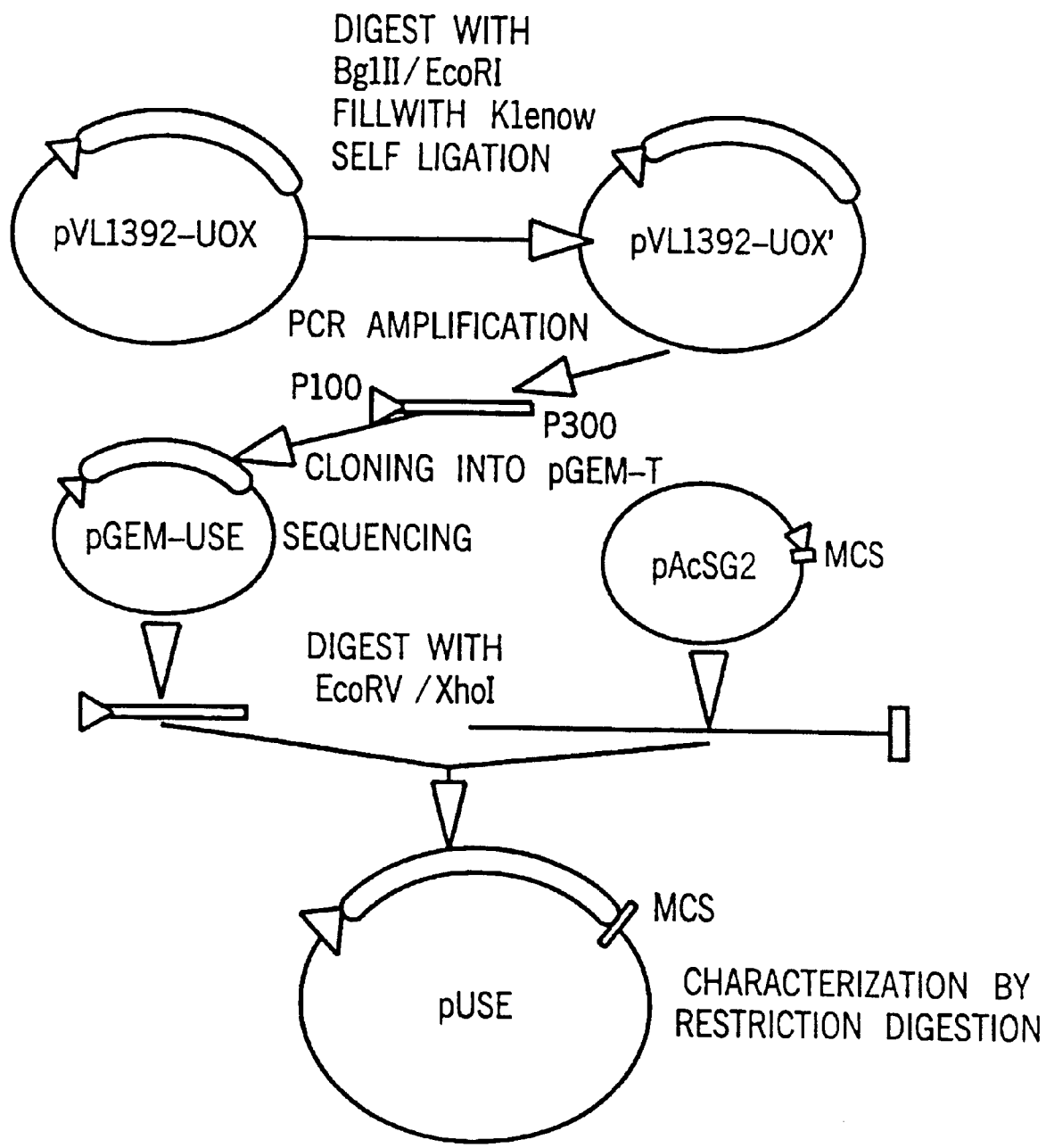
FIG. 2. schematically represents the construction of a vector, designated pUSE, which carries the coding for the insoluble protein tag, uricase (IPTu), which is illustrative of a tag useful in practicing the present invention.

Turning to the drawings, FIG. 2 illustrates the preparation of the vector pUSE by the technique of first cloning a uricase coding fragment in a baculovirus transfer vector pVL1392. Extra linker sequences between BglII and EcoRI were removed resulting in a modified plasmid pVL1392-UOX'. The uricase coding sequences together with baculovirus polyhedrin promoter sequences were then amplified by PCR. The amplified fragment was cloned into pGEM-T vector, and sequenced. The fragment was then cloned into the EcoRV and XhoI site of pAcSG2 plasmid to produce the pUSE vector.

Figure 3:
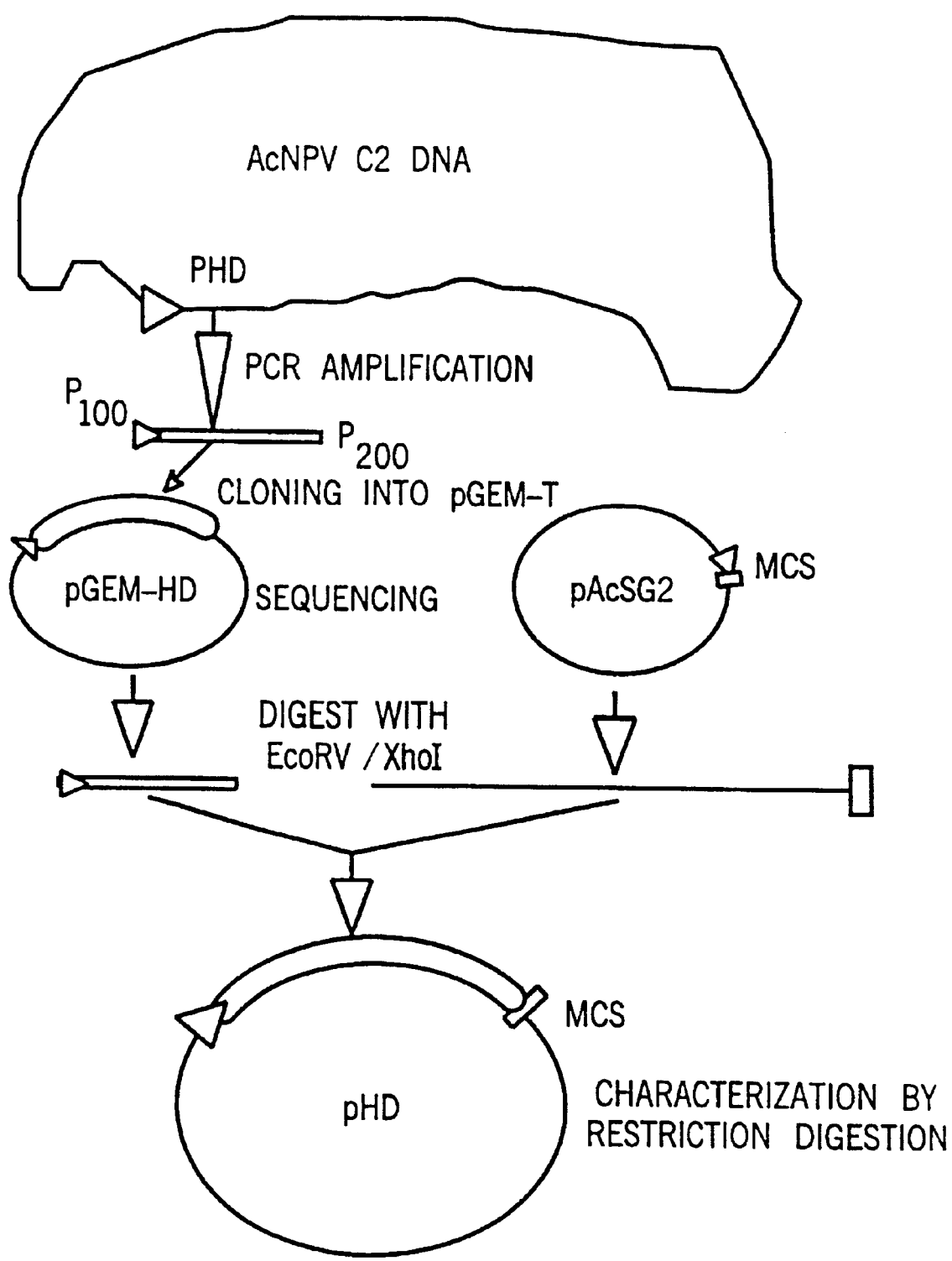
FIG. 3 schematically represents the construction of the vector, designated pHD, which carries the coding for the insoluble tag, baculovirus polyhedrin (IPTp), which is illustrative of another tag useful in practicing the present invention.

Turning to FIG. 3, the construction of the pHD vector is illustrated. The polyhedrin coding sequences together with the polyhedrin promoter sequences were amplified by PCR from wild type AcNPV viral DNA. The amplified fragment was cloned into pGEM-T vector, and sequenced to confirm the authenticity. The fragment was then cloned into the EcoRV and XhoI site of pAcSG2 plasmid to produce the pHD vector.

The following Example I illustrates in more detail the preparation of the vectors which carry the DNA sequence for the insoluble tags, IPTu and IPTp, illustrated in FIGS. 1 and 2.

EXAMPLE I

Preparation of the vector, pUSE: The cDNA fragment coding for rat uricase was obtained by amplifying a rat liver cDNA library (CLONTECH Laboratory, Inc.) using a pair of primers consisting of sequences of GAA TTC CAT TCT TGA AAC CGA ATC TGA (SEQ ID NO:1) and CGG ATC CTA AAG ACA GAG TCT (SEQ ID NO:2) according to GenBank Database M24396 (Alvares et al. 1989). The amplification was performed by adding 1 ul of the cDNA library stock into 49 ul of $H_2O$ containing 50 pmol of each primer and further mixed with 50 ul of PCR master (BOEHRINGER MANNHEIM). The reaction was heated at 95° C. for 2 minutes, and followed by incubations at 60° C. for 1 minute, 68° C. for 1 minute, 95° C. for 30 seconds for a total of 30 cycles. At the end of amplification, the reaction was incubated at 68° C. for an additional 10 minutes, the amplified product was analyzed by electrophoresis on a 1% agarose gel.

A 1.3 kb fragment coding for rat uricase was recovered from the gel and subcloned into a pGEM-T vector using the pGEM-T cloning kit from Promega Corporation. The sequence of the insert was confirmed as rat uricase by DNA sequencing analysis provided by Ana-Gen Technologies Inc. The fragment cloned in pGEM-T vector was further subcloned into a baculovirus transfer vector pVL1392 (PharMingen) between EcoRI and BamHI sites. The resulting plasmid is named as pVL1392-UOX (see FIG. 2).

Subsequently for more convenient operation, the sequences between BglII and EcoRI sites in the vector were removed by double digestion, filling, and relegation. The resulting plasmid, PVL1392-UOX', was used for further PCR amplification using a pair of primers (ACT AAT ATC ACA AAC TGG AAA TGT CTA TCA ATA (SEQ ID NO:3) and GAA TTC CTC GAG CTT ATC GTC ATC GTC GTG ATG GTG ATG GTG ATG CAG CCT GGA AGG CAG CTT CCT CCT CAC CGT CCC (SEQ ID NO:4)) to insert a six Histidine tag and an enterokinase recognition site.

The PCR amplified fragment was first cloned into pGEM-T vector, and verified by restriction digestion and sequencing (service provided Ana-gene Technology, INC.). The fragment was then released from the pGEM-T vector by digestion with EcoRV and XhoI, and inserted into the same sites of pAcSG2, a baculovirus transfer vector from Pharmingen. The final plasmid was characterized by restriction enzyme digestion as pUSE.

Preparation of the vector, pHD: Construction of this insoluble protein tag vector was accomplished using a procedure similar to that for pUSE. Wild type Baculovirus AcNPV C2 DNA (from PharMingen) was amplified using a pair of primers (ACT AAT ATC ACA TGG AAA TGT CTA TCA ATA (SEQ ID NO:5) and GAA TTC CTC GAG CTT ATC GTC ATC GTC GTG ATG GTG ATG GTG ATG ATA CGC CGG ACC AGT GAA CAG AGG TGC GTC TGG (SEQ ID NO:6)) according to GenBank database M25054. The amplification was performed by adding 0.1 µg of the Baculovirus DNA in 50 ul of H₂0 containing 50 pmol of each primer and further mixed with 50 ul of PCR master (BOEHRINGER MANNHEIM). The reaction was heated at 95° C. for 2 minutes, and followed by incubations at 60° C. for 1 minute, 68° C. for 1 minute, 95° C. for 30 seconds for a total of 30 cycles. The PCR amplified fragment was first cloned into pGEM-T vector, and verified by restriction digestion and sequencing (service provided Ana-gene Technology, INC.). The EcoRV and XhoI fragment was then released from the pGEM-T vector, and inserted into pAcSG2, a Baculovirus transfer vector from Pharmingen. The final plasmid was characterized by restriction enzyme digestion as pHD.

Figure 4:
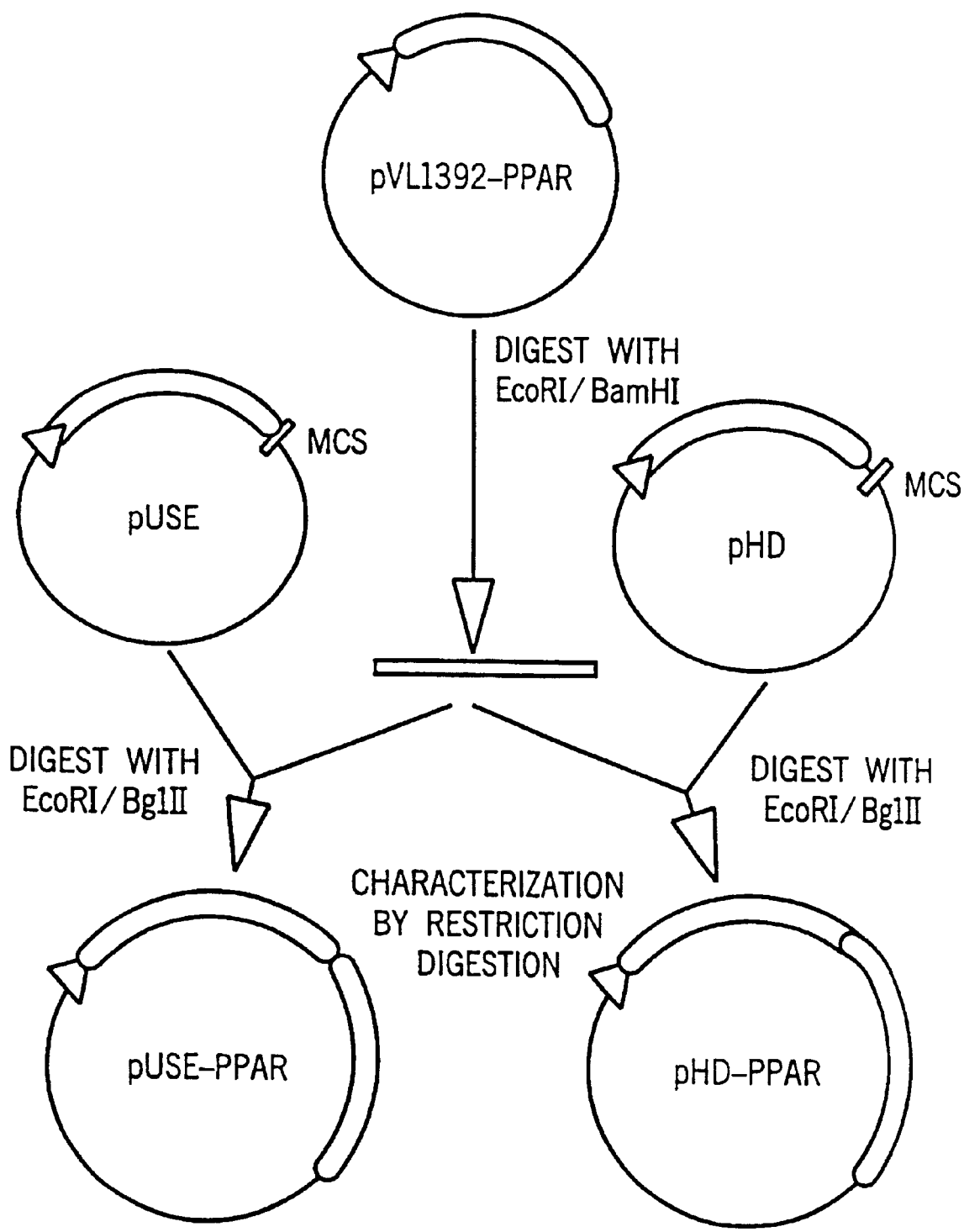
FIG. 4 schematically represents the construction of expression vectors for fusion products containing, as the protein of interest, the nuclear hormone receptor, rat peroxisome proliferator-activated receptor (PPAR), and the tags identified in FIGS. 2 and 3. PPAR is an important transcription factor which regulates gene expression in mammalian cells.

Turning again to the drawings, FIG. 4 illustrates the use of the insoluble tag plasmids prepared above for the construction of transfer vectors which contain coding sequences for the tags and the protein of interest, rat peroxisome proliferator-activated receptor (PPAR). As shown, the fragment coding for the PPAR was first cloned in a baculovirus transfer vector pVL1392. The sequences between EcoRI and BamHI sites were released from pVL1392-PPAR and subcloned into the same sites of pUSE and pHD, respectively. The resulting plasmids, pUSE-PPAR and pHD-PPAR, were characterized by various restriction enzyme digestion and used, as described hereafter in Example III for cotransfection with Baculo-Gold™ baculovirus DNA into insect Sf9 cells.

EXAMPLE II

Construction of Pvl1392-PPAR: The rat peroxisome proliferator-activated receptor (PPAR) alpha coding sequence was obtained by amplification of the same rat liver cDNA library using a pair of primers (AAT GCG GCC GCT ATG CAT CAC CAT CAC CAT CAC ATG GTG GAC ACA GAG AGC CCC (SEQ ID NO:7) and AGC CCG GGG GAT CCG ATC AGT ACA TGT CTC TGT ATA (SEQ ID NO:8)) according to the GenBank database (M88592). The amplification was performed by adding 1 ul of the cDNA library stock into 49 ul of water containing 50 pmol of each primer and further mixed with 50 ul of PCR master (BOEHRINGER MANNHEIM). The reaction was heated at 95° C. for 2 minutes, and followed by incubations at 60° C. for 1 minute, 68° C. for 1 minute, 95° C. for 30 seconds for a total of 30 cycles. Amplified fragment was first cloned into pGEM-T vector (Promega), sequenced, and subcloned into Not I and EcoR I sites of Baculovirus transfer vector pVL-1392 (PharMingen).

Construction of the vectors, pUSE-PPAR and pHD-PPAR: The cDNA fragment encoding rat PPAR alpha was released from pVL1392-PPAR by digestion with the restriction enzymes, EcoRI and BamHI. The fragment, with the same open reading frame, was subcloned into EcoRI and BglII sites of pUSE and pHD, respectively. The resulting plasmids, pUSE-PPAR and pHD-PPAR, were characterized by restriction enzyme digestion with EcoRV/BglII, EcoRV/PstI, and EcoRV/HindIII. The inserts were correct in size and orientation.

In order to demonstrate and compare the expression level of the vectors prepared above (pUSE, pHD, pUSE-PPAR, pHD-PPAR and pVL1292-PPAR) and to illustrate other advantages of the present invention, linearized baculovirus DNA was used to generate recombinant viruses from these constructs and to infect insect Sf9 cells. Example III illustrates the preparation of the recombinant baculoviruses and Example IV illustrates the use of these recombinant viruses in the production of proteins, including the fusion products prepared according to the present invention.

As described above and in Example III, with insect cells the vector was introduced into the cells with linearized baculovirus DNA by means of co-transfection. Where, however, the host cell is another eukaryotic cell such as mammalian or if the host cell is prokaryotic such as bacteria then the construct vectors can be directly introduced into the host cell by well known techniques.

EXAMPLE III

Co-transfection of above constructs with linearized DNA into insect Sf9 cells: Insect Sf9 cells in monolayer cultures were grown in Grace medium containing 10% Fetal Bovine Serum (GIBCO-BRL). For each transfection, a 60 mm tissue culture plate was seeded with 2×10⁶ Sf9 cells and kept at room temperature for 30 minutes. A mixture of 0.5 ug of linear baculovirus DNA (BaculoGold™ DNA from PharMingen) and 5 ug of plasmid DNA (i.e., pUSE, pUSE-PPAR, pHD, pHD-PPAR, and pVL1392-PPAR) was added into 1 ml of Transfection Buffer B (125 mM Hepes, pH 7.1, 125 mM CaCl2, 140 mM NaCl). The DNA/Transfection Buffer B solution was further added into 1 ml of Grace medium in the tissue culture plate drop-by-drop and incubated at 27° C. for 4 hours. At the end, the transfection solution was replaced by 4 ml of fresh Grace medium and the plate was kept at 27° C. for four days.

Purification of the recombinant virus by plaque assay: Four days after co-transfection, the supernatant containing recombinant virus from the co-transfected plates were collected and diluted 1:10, 1:100, 1:1,000, 1:10,000, and 1:100, 000, respectively, with Grace medium. For infection, 2 ml of each of the dilutions were added in a 60 mm tissue culture plate containing 2×10⁶ Sf9 cells and incubated at 27° C. for 1 hour. After infection, a mixture of 2% SeaPlaque agarose (from FMC) melted in water at 65° C. and 2×Grace medium containing 20% FBS at room temperature was overlayed on top of the infected cells and the plate was kept at 27° C. under humid conditions. For each of the constructs (e.g. pUSE, pUSE-PPAR, pHD, pHD-PPAR, and pVL1392-PPAR), four independent plaques were individually picked up using a 1 ml pipette tip and individually resuspended in 200 ul of Grace medium containing 10% FBS.

Amplification of the plaque purified recombinant viruses: A 24 well cell culture plate (from Corning) was seeded with 2×10⁵ Sf9 cells in each well and plaques resuspended in 200 ul of the Grace medium were used to infect the cells. Four days after infection, the media were collected and used to infect 6×10⁶ Sf9 cells seeded in 250 ml cell culture flasks. The amplified viral stocks containing approximately 3×10⁸ PFU/ml were collected four days after infection and stored at 4° C. for further experiments. The remaining infected cells were assayed for recombinant protein expression by SDS-PAGE analysis using a precasted 4–20% gradient gel (Novex). One recombinant baculovirus clone was chosen from these four plaques to represent the original plasmid construct and used for subsequent experiments.

EXAMPLE IV

Figure 5:
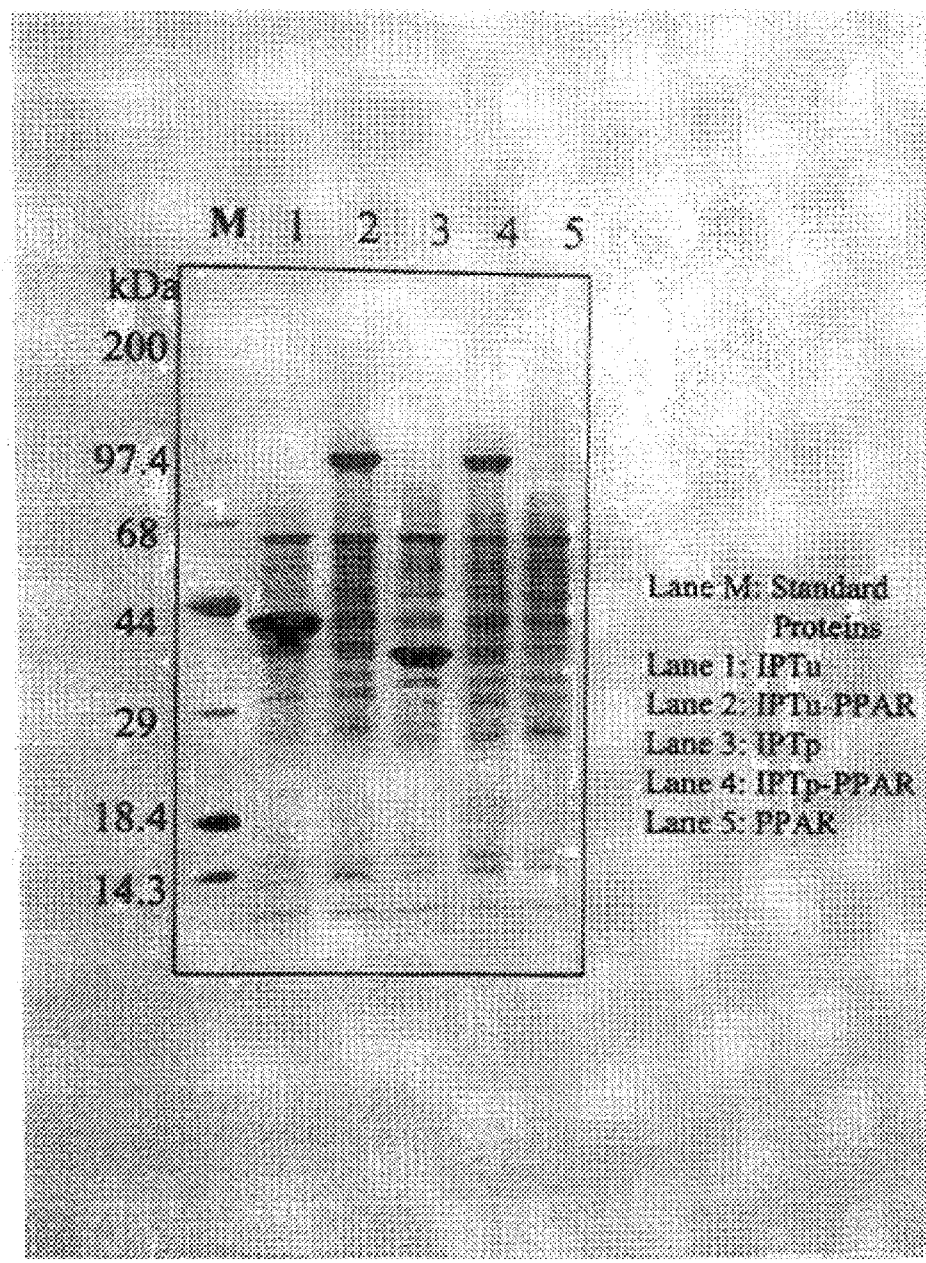
FIG. 5 represents SDS-PAGE analysis of the expression of the insoluble protein tags IPTu and IPTp alone and with their soluble fusion partner PPAR in insect Sf9 cells infected with recombinant baculoviruses generated from pUSE, pUSE-PPAR, pHD, pHD-PPAR, and pVL1392-PPAR, respectively. pVL1392 is a baculovirus transfer vector uniformly used in the preparation of the IPT vectors described herein. The pVL1392-PPAR vector functions as a control in indicating efficiency of protein expression.

Expression of Fusion Protein (IPT-PPAR) in Insect Cells: The recombinant baculoviruses obtained as above described from the constructs of pUSE, pUSE-PPAR, pHD, pHD-PPAR, and pVL1392-PPAR were used to express the uricase (35 kDa) tag, the uricase-PPAR fusion protein (90 kDa), the polyhedrin tag (30 kDa), the polyhedrin-PPAR fusion protein (85 kDa), and PPAR (55 kDa), respectively. To compare the expression, 200 ul of the viral stock containing 3×10[8] PFU/ml were used to infect Sf9 cells grown in a 250 ml tissue culture flask at 80% confluence. Three days (72 hours) after infection, the infected cells were washed once with phosphate-buffered saline, lysed with SDS-PAGE sample buffer and then analyzed by SDS-PAGE using a precasted 4–20% SDS-PAGE gel (Novex). After electrophoresis, the gel was stained with Coomassie Blue and the results are shown in FIG. 5. A dominant recombinant protein band representing uricase (lane 1) tag, uricase-PPAR fusion protein (lane 2), polyhedrin tag (lane 3), polyhedrin-PPAR fusion protein (lane 4), respectively, were observed in the insect cell lysates (about 20–50% of the total cellular protein). In contrast, with PPAR alone, absent either insoluble tag (lane 5), no significant recombinant protein accumulations were observed. The recombinant PPAR protein, the expression of which is known to be very difficult, can only be detected by immunoblotting. The expression of PPAR in insect cells was reported at the low level of 10 mg/10[9] cells (Proc. Natl. Acad. Sci. USA, 90, 1440–1444). With uricase and polyhedrin tag, the expression reached a level of 500 and 100 mg/10[9] cells, respectively. Thus, the expression of PPAR was increased 10–50 fold by uricase and polyhedrin tag.

Example V illustrates purification of the fusion proteins expressed above by the one-step procedure of the present invention.

EXAMPLE V

Figure 6:
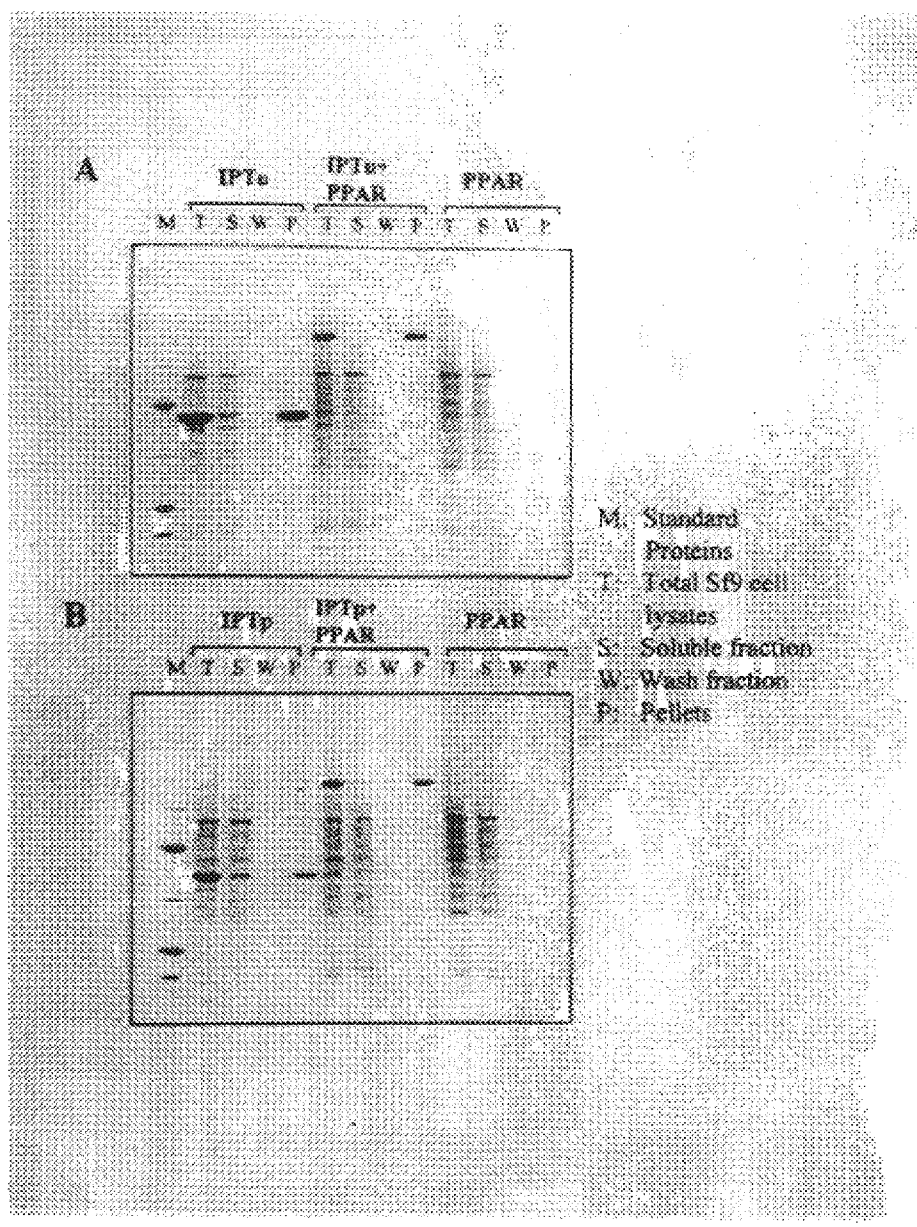
FIG. 6 represents an SDS-PAGE analysis of a one-step procedure for purification of PPAR fused to IPTu or IPTp tags. Uricase (IPTu, panel A) and polyhedrin (IPTp, panel B) alone or fused to PPAR were expressed in insect cells and purified by a one-step "spin-down" procedure. Lanes: T, total cell lysates; S, supernatant; W, washed supernatant; P, pellets; M, molecular weight standard.

The recombinant proteins, 0.5 g wet total protein of insect cells infected with respective recombinant baculovirus (prepared as in Example III) were resuspended in 5 ml of B-PER Reagent (Pierce Chemical Company) to lyse the cells according to manufacturer's instructions. The suspensions were stirred for 1 hour at 4° C. and then centrifuged at 12,000×g for 30 min and the pellets were washed once with the same reagent to eliminate possible contamination from membrane proteins. In order to obtain activity, the final pellets were solubilized by increasing pH to 11 by stirring with 0.1 M $Na_2CO_3$ for 1 hour. Samples from each step were taken and analyzed by SDS-PAGE. As shown in FIG. 6, IPTu, IPTu-PPAR, IPTp, and IPTp-PPAR were the dominant proteins in the total cellular lysates.

As shown, after centrifugation, the respective purified proteins were removed from the supernatants. The washing step with the same reagent further removes possible contaminants. The recombinant fusion protein remains as a pellet and the purity is greater than 90% by this spin-down procedure as judged by SDS-PAGE analysis. Fusion proteins and tags exhibit similar patterns indicating that uricase and polyhedrin are capable of pulling down their fusion partner.

EXAMPLE VI

Detection of the IPTu-PPAR Fusion Protein by Measuring Uricase Activity: An additional benefit provided by the uricase tag is that the fusion protein can be monitored by a simple spectrophotometric assay. The total protein lysates, supernatant, washed supernatant, and final purified IPTu-PPAR fusion protein were 1:1 diluted in 0.1 M Glycine (pH 9.4). To detect the uricase activity, 100 ul of the diluted samples were incubated with 100 ul of uric acid (15 mg/ml in 0.1 M Glycine) at 37° C. for 1 hour. At the end of incubation, 20 ul of 50% TCA solution was added into the reaction and the proteins were removed from the sample by spin at 15,000 RPM with a microcentrifuge for 5 minutes. The supernatants were collected and added into 1 ml of 0.1 M Glycine. The absorption at OD 295 was recorded by a HITACHI U2000 spectrophotometer. As shown in FIG. 7, most of the uricase activity, by the illustrated disappearance of uric acid absorbance at 295, is retained in the pellet fraction. Thus uricase served as a dual functional tag for one-step purification and easy detection.

The following Example VII illustrates a procedure according to this invention for removing the insoluble tag, IPTu, from the protein, PPAR, and the subsequent recovery of the protein.

EXAMPLE VII

Approximately 20 ug of IPTu-PPAR fusion protein purified by the one-step procedure and solubilized in 20 ul of 0.1 M $Na_2CO_3$ (pH 11), as described in Example V, were dialyzed against 50 ml of the dialysis buffer containing 50 mM Tris-HCl (pH8.8), 100 mM NaCl, and 5 mM DTT overnight at 4° C. After dialysis, the sample was digested with enterokinase to cleave off the tag by mixing with 3 ul of 10× EKMax Buffer and 4 ul of EKMax (from Invitrogen) at a total volume of 30 ul and incubated at 37° C. for 16 hours. After digestion, 10 ul of 200 mM Tris.HCl (pH 6.8) were added into the digested sample to adjust the pH to 7.5. At this neutral pH, the uricase tag is insoluble and precipitates out of the solution. The tag and any undigested fusion protein were removed by centrifugation at 15 k rpm for 15 minutes and approximately 8 ug of soluble PPAR were obtained by this procedure. The same procedure is also applicable with respect to the IPTp-PPAR fusion protein.

While the invention has been illustrated above with respect to PPAR as the soluble protein of interest, it is to be understood that the invention is applicable to other proteins which, as expressed, are soluble in aqueous lysate solutions, preferably solutions under physiological conditions, e.g., a pH of 7–8 and a temperature of 20°–37° C. Accordingly, many of those soluble proteins which have heretofore been separated from their lysate solutions in fused product form using conventional tags can now be more conveniently separated utilizing insoluble tags as illustrated in the present invention. Thus, lysate solutions at a pH and/or temperature other than that specified above may also be useful so long as the protein is soluble and the tag is insoluble.

Figure 9:
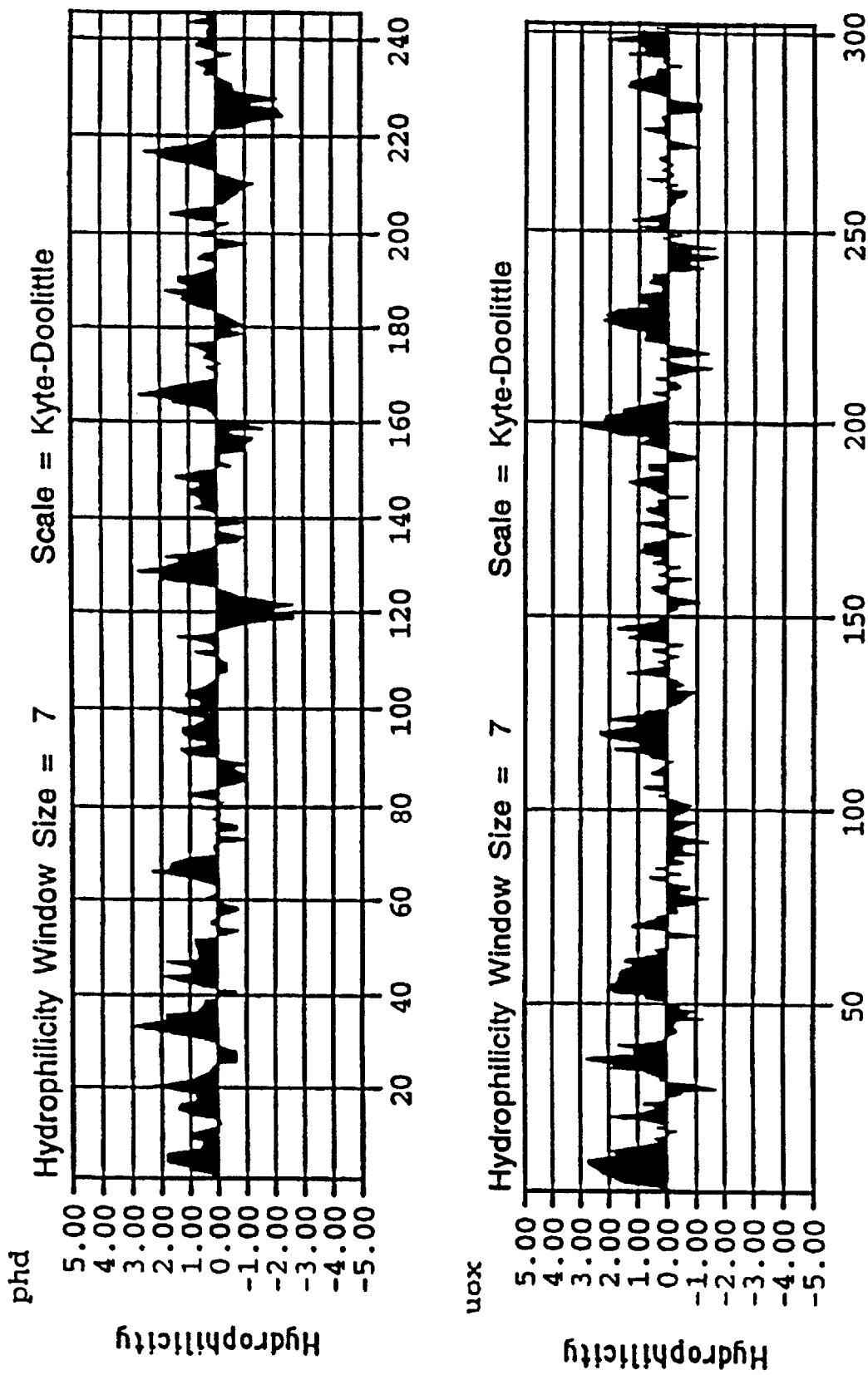
FIG. 9 illustrates the comparison of hydrophilicity between uricase and polyhedrin, again accomplished using the MACVECTOR program from Oxford Molecular Group.

In like fashion, while uricase and polyhedron have been shown as useful as particularly useful insoluble tags, the invention is also applicable to other tags which, as expressed, are insoluble in the chosen aqueous lysate solutions, preferably under physiological conditions. In particular, proteins similar to uricase and polyhedrin regions are considered to demonstrate the desired insolubility to be useful as tags for the purposes of the present invention. As shown in FIG. 8 (SEQ ID NOs:9 and 10), uricase and polyhedrin have a 15% identify in amino acid sequences (the "*" symbol) and a 12% similarity (the "." symbol). Accordingly, proteins having a combined identity and similarity in amino acid sequences to uricase or polyhedrin of at least 25% and, preferably, at least 27% are considered to be useful herein as insoluble tags. As shown in FIG. 9, there is also a similarity in hydrophilicity between uricase and polyhedrin. While not quantitated, similarity in this characteristic is also considered to be useful in the selection of an insoluble proteinaceous tag. Accordingly, truncated versions of uricase and polyhedrin which are insoluble in the lysate solution are also deemed useful.

What is claimed is:

1. In a process for the preparation of a recombinantly expressed fusion product comprising a proteinaceous tag and a soluble protein of interest and the separation of said fusion product from the host cell in which it is expressed comprising the steps of, (1) preparing a vector containing a DNA sequence coding for the protein of interest and the DNA sequence coding for the tag, (2) introducing said vector into a host cell and expressing the fusion product, (3) lysing the host cell with a lysate solution, and (4) separating the fusion product from the host cell lysate solution, the improvement wherein the tag and in turn the fusion product is insoluble in the host cell lysate solution and said fusion product is precipitated from the lysate solution and is substantially separated from host cell proteins by centrifugation or filtration, wherein the protein of interest is (PPAR) peroxisome proliferator-activated receptor and wherein the proteinaceous tag is uricase.

* * * * *

SEQUENCE LISTING

<160> NUMBER OF SEQ ID NOS: 10

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: DNA
      sequence of a sense primer used for amplification of rat urate
      oxidase

<400> SEQUENCE: 1
gaattccatt cttgaaaccg aatctga                                      7

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: DNA
      sequence of an antisense primer used for amplifcation of rat urate
      oxidase

<400> SEQUENCE: 2
cggatcctaa agacagagtc t                                           21

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: DNA
      sequence of a sense primer used for construction of pUSE

<400> SEQUENCE: 3
actaatatca caaactggaa atgtctatca ata                              33

<210> SEQ ID NO 4
<211> LENGTH: 78
<212> TYPE: DNA
<213> ORGANISM: Artificial Sequence
<220> FEATURE:
<223> OTHER INFORMATION: Description of Artificial Sequence: DNA
      sequence of an antisense primer used for construction of pUSE

<400> SEQUENCE: 4
gaattcctcg agcttatcgt catcgtcgtg atggtgatgg tgatgcagcc tggaaggcag   60
cttcctcctc accgtccc                                               78

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: DNA
      sequence of a sense primer used for construction of pHD

<400> SEQUENCE: 5
actaatatca catggaaatg tctatcaata                                  30

<210> SEQ ID NO 6
<211> LENGTH: 78
<212> TYPE: DNA
<213> ORGANISM: Artificial Sequence
<220> FEATURE:

<223> OTHER INFORMATION: Description of Artificial Sequence: DNA
      sequence of a sense primer used for construction of pHD

<400> SEQUENCE: 6
gaattcctcg agcttatcgt catcgtcgtg atggtgatgg tgatgatacg ccggaccagt      60
gaacagaggt gcgtctgg                                                   78

<210> SEQ ID NO 7
<211> LENGTH: 60
<212> TYPE: DNA
<213> ORGANISM: Artificial Sequence
<220> FEATURE:
<223> OTHER INFORMATION: Description of Artificial Sequence: DNA
      sequence of a sense primer used for amplification of PPAR

<400> SEQUENCE: 7
aatgcggccg ctatgcatca ccatcaccat caccatcaca tggtggacac agagagcccc     60

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence: DNA
      sequence of an antisense primer used for amplification of PPAR

<400> SEQUENCE: 8
agcccggggg atccgatcag tacatgtctc tgtaga                               36

<210> SEQ ID NO 9
<211> LENGTH: 245
<212> TYPE: PRT
<213> ORGANISM: Baculovirus transfer vector pBacPAK-His1

<400> SEQUENCE: 9

Met Pro Asp Tyr Ser Tyr Arg Pro Thr Ile Gly Arg Thr Tyr Val Tyr
 1               5                  10                  15

Asp Asn Lys Tyr Tyr Lys Asn Leu Gly Ala Val Ile Lys Asn Ala Lys
            20                  25                  30

Arg Lys Lys His Phe Ala Glu His Glu Ile Glu Glu Ala Thr Leu Asp
        35                  40                  45

Pro Leu Asp Asn Tyr Leu Val Ala Glu Asp Pro Phe Leu Gly Pro Gly
    50                  55                  60

Lys Asn Gln Lys Leu Thr Leu Phe Lys Glu Ile Arg Asn Val Lys Pro
65                  70                  75                  80

Asp Thr Met Lys Leu Val Val Gly Trp Lys Gly Lys Glu Phe Tyr Arg
                85                  90                  95

Glu Thr Trp Thr Arg Phe Met Glu Asp Ser Phe Pro Ile Val Asn Asp
            100                 105                 110

Gln Glu Val Met Asp Val Phe Leu Val Val Asn Met Arg Pro Thr Arg
        115                 120                 125

Pro Asn Arg Cys Tyr Lys Phe Leu Ala Gln His Ala Leu Arg Cys Asp
    130                 135                 140

Pro Asp Tyr Val Pro His Asp Val Ile Arg Ile Val Glu Pro Ser Trp
145                 150                 155                 160

Val Gly Ser Asn Asn Glu Tyr Arg Ile Ser Leu Ala Lys Lys Gly Gly
                165                 170                 175

Gly Cys Pro Ile Met Asn Leu His Ser Glu Tyr Thr Asn Ser Phe Glu
            180                 185                 190

Gln Phe Ile Asp Arg Val Ile Trp Glu Asn Phe Tyr Lys Pro Ile Val
            195                 200                 205

Tyr Ile Gly Thr Asp Ser Ala Glu Glu Glu Ile Leu Leu Glu Val
        210                 215                 220

Ser Leu Val Phe Lys Val Lys Glu Phe Ala Pro Asp Ala Pro Leu Phe
225                 230                 235                 240

Thr Gly Pro Ala Tyr
                245

<210> SEQ ID NO 10
<211> LENGTH: 303
<212> TYPE: PRT
<213> ORGANISM: Rattus rattus

<400> SEQUENCE: 10

Met Ala His Tyr His Asp Asp Tyr Gly Lys Asn Asp Glu Val Glu Phe
1               5                   10                  15

Val Arg Thr Gly Tyr Gly Lys Asp Met Val Lys Val Leu His Ile Gln
                20                  25                  30

Arg Asp Gly Lys Tyr His Ser Ile Lys Glu Val Ala Thr Ser Val Gln
            35                  40                  45

Leu Thr Leu Arg Ser Lys Lys Asp Tyr Leu His Gly Asp Asn Ser Asp
    50                  55                  60

Ile Ile Pro Thr Asp Thr Ile Lys Asn Thr Val His Val Leu Ala Lys
65                  70                  75                  80

Phe Lys Gly Ile Lys Ser Ile Glu Thr Phe Ala Met Asn Ile Cys Glu
                85                  90                  95

His Phe Leu Ser Ser Phe Ser His Val Thr Arg Ala His Val His Val
            100                 105                 110

Glu Glu Val Pro Trp Lys Arg Phe Glu Lys Asn Gly Val Lys His Val
        115                 120                 125

His Ala Phe Ile His Thr Pro Thr Gly Thr His Phe Cys Asp Val Glu
130                 135                 140

Gln Val Arg Asn Gly Pro Pro Ile Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Gln
            180                 185                 190

Val Tyr Cys Lys Trp Arg Tyr Gln Asn Arg Asp Val Asp Phe Glu Ala
        195                 200                 205

Thr Trp Gly Ala Val Arg Asp Ile Val Leu Lys Lys Phe Ala Gly Pro
    210                 215                 220

Tyr Asp Arg Gly Glu Tyr Ser Pro Ser Val Gln Lys Thr Leu Tyr Asp
225                 230                 235                 240

Ile Gln Val Leu Thr Leu Ser Gln Leu Pro Glu Ile Glu Asp Met Glu
                245                 250                 255

Ile Ser Leu Pro Asn Ile His Tyr Phe Asn Ile Asp Met Ser Lys Met
            260                 265                 270

Gly Leu Ile Asn Lys Glu Glu Val Leu Pro Leu Asp Asn Pro Tyr
        275                 280                 285

Gly Lys Ile Thr Gly Thr Val Arg Arg Lys Leu Pro Ser Arg Leu
290                 295                 300